(12) United States Patent
Kawashima et al.

(10) Patent No.: US 9,944,575 B2
(45) Date of Patent: Apr. 17, 2018

(54) METHANE GAS CONCENTRATION METHOD

(71) Applicant: Osaka Gas Co., Ltd., Osaka-shi (JP)

(72) Inventors: Shota Kawashima, Osaka (JP); Takahisa Utaki, Osaka (JP)

(73) Assignee: Osaka Gas Co., Ltd., Osaka (JP)

( * ) Notice: Subject to any disclaimer, the term of this patent is extended or adjusted under 35 U.S.C. 154(b) by 44 days.

(21) Appl. No.: 14/772,489

(22) PCT Filed: Feb. 27, 2014

(86) PCT No.: PCT/JP2014/054844
§ 371 (c)(1),
(2) Date: Sep. 3, 2015

(87) PCT Pub. No.: WO2014/136645
PCT Pub. Date: Sep. 12, 2014

(65) Prior Publication Data
US 2016/0016866 A1 Jan. 21, 2016

(30) Foreign Application Priority Data
Mar. 4, 2013 (JP) .................. 2013-041898

(51) Int. Cl.
*C07C 7/12* (2006.01)
*C10L 3/10* (2006.01)
(Continued)

(52) U.S. Cl.
CPC .............. *C07C 7/12* (2013.01); *B01D 53/047* (2013.01); *B01J 20/103* (2013.01); *B01J 20/18* (2013.01);
(Continued)

(58) Field of Classification Search
CPC .. C07C 7/12; C07C 7/005; C07C 7/13; C10L 3/101; B01D 53/047; B01J 20/3416;
(Continued)

(56) References Cited

U.S. PATENT DOCUMENTS 5,089,048 A  2/1992  Knoblauch et al.
8,545,601 B2  10/2013  Song
(Continued)

FOREIGN PATENT DOCUMENTS

CN  1850319 A  10/2006
CN  102821826 A  12/2012
(Continued)

*Primary Examiner* — Brian A McCaig
*Assistant Examiner* — Jason Y Chong
(74) *Attorney, Agent, or Firm* — The Webb Law Firm

(57) ABSTRACT

Adsorption towers are filled with adsorbents that adsorb methane gas in coal mine gas and perform a PSA cycle. For each of adsorption towers, a plurality of different pressure states of the internal pressure of the adsorption tower are set as an intermediate pressure state. As a pressure equalization step, an initial pressure equalization step of transferring the gas in one of the adsorption towers that is in a high pressure state to another one of the adsorption towers that is in an intermediate pressure state, and a final pressure equalization step of transferring the gas in one of the adsorption towers that is in the high pressure-side intermediate pressure state to another one of the adsorption towers that is in the low pressure state are performed.

4 Claims, 10 Drawing Sheets

(51) Int. Cl.
*B01J 20/18* (2006.01)
*B01J 20/20* (2006.01)
*B01J 20/22* (2006.01)
*B01J 20/34* (2006.01)
*B01J 20/28* (2006.01)
*B01J 20/10* (2006.01)
*C07C 7/13* (2006.01)
*B01D 53/047* (2006.01)
*C07C 7/00* (2006.01)

(52) U.S. Cl.
CPC ............. *B01J 20/20* (2013.01); *B01J 20/223* (2013.01); *B01J 20/2808* (2013.01); *B01J 20/3416* (2013.01); *B01J 20/3425* (2013.01); *B01J 20/3433* (2013.01); *B01J 20/3491* (2013.01); *C07C 7/005* (2013.01); *C07C 7/13* (2013.01); *C10L 3/101* (2013.01); *B01D 2253/102* (2013.01); *B01D 2253/106* (2013.01); *B01D 2253/108* (2013.01); *B01D 2253/204* (2013.01); *B01D 2257/7025* (2013.01); *B01D 2259/404* (2013.01); *B01D 2259/40071* (2013.01); *B01D 2259/40075* (2013.01); *C10L 2290/542* (2013.01); *C10L 2290/58* (2013.01); *Y02C 20/20* (2013.01); *Y02P 20/156* (2015.11)

(58) Field of Classification Search
CPC .. B01J 20/3425; B01J 20/2808; B01J 20/103; B01J 20/223; B01J 20/3491; B01J 20/3433; B01J 20/18; B01J 20/20
See application file for complete search history.

(56) References Cited

U.S. PATENT DOCUMENTS

| 8,747,522 | B2 | 6/2014 | Guenther |
| 2004/0074388 | A1 | 4/2004 | Lomax, Jr. |
| 2013/0125466 | A1 | 5/2013 | Utaki et al. |

FOREIGN PATENT DOCUMENTS

| CN | 102861499 | A | 1/2013 |
| DE | 102010011347 | A1 | 9/2011 |
| EA | 012820 | B1 | 12/2009 |
| JP | 5512295 | B1 | 4/1980 |
| JP | 2503553 | A | 10/1990 |
| JP | 58198591 | A | 11/1993 |
| JP | 2006501996 | A | 1/2006 |
| PL | 163229 | B1 | 4/1992 |
| PL | 318330 | A1 | 8/1998 |
| PL | 176332 | B1 | 5/1999 |
| WO | 2011118406 | A1 | 9/2011 |

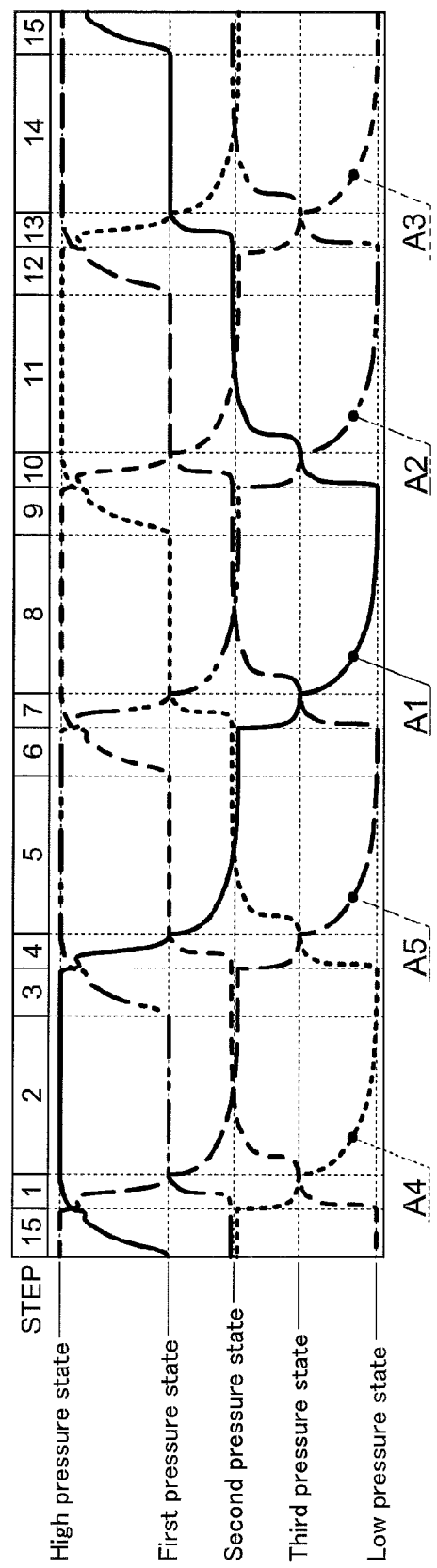

METHANE GAS CONCENTRATION METHOD

CROSS-REFERENCE TO RELATED APPLICATIONS

This application is the U.S. national phase of International Application No. PCT/JP2014/054844 filed Feb. 27, 2014, and claims priority to Japanese Patent Application No. 2013-041898 filed Mar. 4, 2013, the disclosures of which are hereby incorporated in their entirety by reference.

TECHNICAL FIELD

The present invention relates to a methane gas concentration method including:

providing four or more adsorption towers each filled with an adsorbent that adsorbs methane gas; and performing, for each of the adsorption towers, a PSA (Pressure Swing Adsorption) cycle of repeating in order:

an adsorption step of receiving supply of the methane gas in a high pressure state near atmospheric pressure, and adsorbing the methane gas on the adsorbent;

a pressure equalization (depressurizing) step of transferring the gas in the adsorption tower that has finished the adsorption step and is in the high pressure state to another adsorption tower in a lower pressure state so as to bring the inside of the adsorption tower into an intermediate pressure state;

a decompression step of, after the internal pressure of the tower has been lowered by the pressure equalization (depressurizing) step, further decompressing the adsorbent to a low pressure state so as to desorb the methane gas adsorbed on the adsorbent, and recovering that methane gas;

a pressure equalization (pressurizing) step of, after finishing the decompression step, receiving the gas from another adsorption tower that is in a higher pressure state so as to bring the inside of the adsorption tower into an intermediate pressure state; and a pressurizing step of, after the internal pressure of the tower has been increased by the pressure equalization (pressurizing) step, further supplying a pressurizing gas into the adsorption tower so as to restore the adsorbent into a high pressure state capable of selectively adsorbing the methane gas.

BACKGROUND ART

In the case of effectively using a flammable gas, it is necessary to separate a gas such as air from a source gas containing the flammable gas, and concentrate the flammable gas to an appropriate concentration range. Various such apparatuses and methods for concentrating a flammable gas have been proposed, and inventions have been proposed in which a gas (so-called coal mine gas) generating from a coal mine in the form of a methane-containing gas is used as a source gas, air (mainly containing nitrogen, oxygen, and carbon dioxide) is separated from the source gas by using an adsorbent, and the methane gas is concentrated for use.

More specifically, Patent Document 1 proposes an invention of an apparatus and a method for concentrating methane gas. According to the invention, with the use of natural zeolite, which has a very slower adsorption rate for methane gas than for nitrogen, as an adsorbent (i.e., with the use of an adsorbent that preferentially adsorbs nitrogen, oxygen, and carbon dioxide to methane gas), coal mine gas is introduced into an adsorption tower filled with the adsorbent by a compressor or the like until a predetermined pressure is reached. Then, nitrogen, oxygen, and carbon dioxide that are contained in the coal mine gas are adsorbed first at the front portion (lower portion) of the adsorbent tower, and methane gas, for which the adsorption rate is slow, is adsorbed at the back portion (upper portion) of the adsorption tower. Further, the methane gas is released from the upper portion of the adsorption tower until it reaches atmospheric pressure.

Thereby, the air can be separated from the coal mine gas as the source gas by using the adsorbent, the methane gas can be concentrated, and the concentrated methane gas can be used as a fuel or the like.

That is, as the PSA cycle, a configuration is conceivable that is provided with a control means for successively performing a flammable gas adsorption step of supplying the source gas to the adsorption tower by a supply and release means, and releasing exhaust gas from the adsorption tower, and a flammable gas desorption step of collecting the flammable gas desorbed by a collecting means.

Further, as such a PSA cycle, it has been considered to perform a pressure equalization step of transferring the gas in the adsorption tower that has finished the adsorption step and is in the high pressure state into another adsorption tower in a lower pressure state so as to bring the inside of the adsorption tower into an intermediate pressure state, and a pressure equalization step of receiving, after finishing the decompression step, the gas from another adsorption tower that is in a higher pressure state so as to bring the inside of the adsorption tower into an intermediate pressure state, thereby improving the efficiency of the energy required for pressurizing and depressurizing in the adsorption towers, and increasing the recovery rate of the gas to be concentrated.

Note that in the present invention, of a pair of adsorption towers that perform the pressure equalization steps, the pressure equalization step performed by the adsorption tower whose internal pressure is lowered by transferring the gas to the other tower is referred to as the pressure equalization (depressurizing) step, and the pressure equalization step performed by the adsorption tower whose internal pressure is increased by receiving the gas from the other tower is referred to as the pressure equalization (pressurizing) step.

In addition, Patent Document 2 further discloses a helium gas concentration method including:

providing four adsorption towers each filled with an adsorbent that adsorbs methane gas and nitrogen; and in the case of performing, for each of the adsorption towers, a PSA cycle of performing:

an adsorption step of receiving supply of a helium-containing methane gas, adsorbing methane gas on the adsorbent, and recovering helium gas;

a pressure equalization (depressurizing) step of transferring the gas in the adsorption tower that has finished the adsorption step and is in the high pressure state to another adsorption tower in a lower pressure state so as to bring the inside of the adsorption tower into an intermediate pressure state;

a decompression step of, after the internal pressure of the tower has been lowered by the pressure equalization (depressurizing) step, further decompressing the adsorbent to a low pressure state so as to desorb the methane gas adsorbed on the adsorbent;

a pressure equalization (pressurizing) step of receiving, after finishing the decompression step, the gas from another adsorption tower that is in a higher pressure state so as to bring the inside of the adsorption tower into an intermediate pressure state; and a pressurizing step of, after the internal pressure of the tower has been increased by the pressure equalization (pressurizing) step, further supplying a pressurizing gas into the adsorption tower so as to restore the adsorbent into a high pressure state capable of selectively adsorbing the methane gas, two different pressure states of the internal pressure of the adsorption tower are set as the intermediate pressure state, the method includes, as the pressure equalization (depressurizing) step, an initial pressure equalization (depressurizing) step of transferring the gas in one of the adsorption towers that is in the high pressure state to another one of the adsorption towers that is in an intermediate pressure state at a pressure lower than the pressure of the one of the adsorption towers so as to bring the pressure in the one of the adsorption towers into a high pressure-side intermediate pressure state, and a final pressure equalization (depressurizing) step of transferring the gas in one of the adsorption towers that is in the high pressure-side intermediate pressure state at a pressure higher than the low pressure state to another one of the adsorption towers that is in the low pressure state so as to bring the pressure in the one of the adsorption towers into a low pressure-side intermediate pressure state, and the pressure equalization (pressurizing) step includes:

an initial pressure equalization (pressurizing) step of receiving the gas in one of the adsorption towers that is in the high pressure-side intermediate pressure state into another one of the adsorption towers that is in the low pressure state so as to bring the pressure in the one of the adsorption towers into the low pressure-side intermediate pressure state; and a final pressure equalization (pressurizing) step of receiving, into one of the adsorption towers that is in the low pressure-side intermediate pressure state, the gas in another one of the adsorption towers that is in the high pressure state so as to bring the pressure in the one of the adsorption towers into the high pressure-side intermediate pressure state.

PRIOR ART DOCUMENTS

Patent Documents

Patent Document 1: JP S58-198591A
Patent Document 2: JP H02-503553W (in particular, FIG. 3)

DISCLOSURE OF THE INVENTION

Problem to be Solved by the Invention

Although the technique disclosed in Patent Document 2 is a technique for recovering the helium gas that is not adsorbed on the adsorbent, it is also a technique for recovering the methane gas adsorbed in the decompression step. Therefore, it can be understood that the technique can be used as a technique for concentrating methane gas contained in coal mine gas, regardless of whether or not helium is contained in the coal mine gas.

However, the above-described technique is a technique for recovering the helium gas that has not been adsorbed on the adsorbent, and therefore, no considerations have been given to the recovery rate or concentration of the recovered methane in the case of recovering the methane adsorbed on the adsorbent. In particular, as for how the technique disclosed in Patent Document 2 should be applied to improve the concentration of the recovered methane, it is difficult to find suitable conditions in a simple manner because the relationship between the concentration of the recovered methane and various parameters such as operating conditions is totally unknown. Also, whether the technique is indeed applicable is questionable.

Therefore, in view of the above-described situations, it is an object of the present invention to provide a methane gas concentration method that can further improve the methane concentration when methane gas is concentrated by PSA.

Means for Solving Problem (Configuration 1)

A characteristic feature of a methane gas concentration method of the present invention for attaining the above-described object lies in a methane gas concentration method including:

providing four or more adsorption towers each filled with an adsorbent that adsorbs methane gas in a methane-containing gas; and performing, for each of the adsorption towers, a PSA cycle of repeating in order:

an adsorption step of receiving supply of the methane-containing gas in a high pressure state near atmospheric pressure from a lower portion of the adsorption tower, adsorbing the methane gas on the adsorbent, and releasing offgas composed mainly of air from an upper portion of the adsorption tower;

a pressure equalization (depressurizing) step of transferring the gas in the adsorption tower that has finished the adsorption step and is in the high pressure state to another adsorption tower in a lower pressure state so as to bring the inside of the adsorption tower into an intermediate pressure state;

a decompression step of, after the internal pressure of the tower has been lowered by the pressure equalization (depressurizing) step, further decompressing the adsorbent to a low pressure state so as to desorb the methane gas adsorbed on the adsorbent, and recovering said methane gas from the lower portion of the adsorption tower;

a pressure equalization (pressurizing) step of receiving, after finishing the decompression step, the gas from another adsorption tower that is in a higher pressure state so as to bring the inside of the adsorption tower into an intermediate pressure state; and a pressurizing step of, after the internal pressure of the tower has been increased by the pressure equalization (pressurizing) step, further supplying a pressurizing air into the adsorption tower from an upper portion of the adsorption tower so as to restore the adsorbent into a high pressure state capable of selectively adsorbing the methane gas, wherein the adsorbent has a property of selectively adsorbing the methane gas contained in the air in the high pressure state near atmospheric pressure and desorbing the adsorbed methane gas in the low pressure state, and a property of preferentially desorbing the air when desorbing the methane gas, a plurality of different pressure states of the internal pressures of the adsorption tower are set as the intermediate pressure state, the method includes, as the pressure equalization (depressurizing) step, an initial pressure equalization (depressurizing) step of transferring the gas in one of the adsorption towers that is in the high pressure state to another one of the adsorption towers that is in an intermediate pressure state at a pressure lower than the pressure of the one of the adsorption towers so as to bring the pressure in the one of the adsorption towers into a high pressure-side intermediate pressure state, and a final pressure equalization (depressurizing) step of transferring the gas in one of the adsorption towers that is in the high pressure-side intermediate pressure state at a pressure higher than the low pressure state to another one of the adsorption towers that is in the low pressure state so as to bring the pressure in the one of the adsorption towers into a low pressure-side intermediate pressure state, the pressure equalization (pressurizing) step includes:

an initial pressure equalization (pressurizing) step of receiving the gas in one of the adsorption towers that is in the high pressure-side intermediate pressure state into another one of the adsorption towers that is in the low pressure state so as to bring the pressure in the one of the adsorption towers into the low pressure-side intermediate pressure state; and a final pressure equalization (pressurizing) step of receiving, into one of the adsorption towers that is in the low pressure-side intermediate pressure state, the gas in another one of the adsorption towers that is in the high pressure state so as to bring the pressure in the one of the adsorption towers into the high pressure-side intermediate pressure state, and the gas is transferred from one of the adsorption towers that performs the pressure equalization (depressurizing) step to another one of the adsorption towers that performs the pressure equalization (pressurizing) step from the upper portion of the one of the adsorption towers to the upper portion of the other one of the adsorption towers.

(Operation and Effect 1)

Since the above-described configuration includes a basic configuration of the above-described conventional flammable gas concentration apparatus, it is possible to concentrate methane gas by adsorbing the methane gas on the adsorption tower, and successively performing the adsorption step and the desorption step.

In the above-described configuration, the adsorbent has the property of selectively adsorbing the methane gas contained in the air in the high pressure state near atmospheric pressure and desorbing the adsorbed methane gas in the low pressure state, and has the property of preferentially desorbing a gas other than the methane gas when desorbing the methane gas in the low pressure state. That is, the adsorbent has such a property that the air starts to be desorbed preferentially to the methane gas at the initial stage after the start of desorption when desorbing the methane gas, but the desorption ratio of the methane gas increases as the desorption operation continues.

Accordingly, when the initial pressure equalization (depressurizing) step is performed after the adsorption step, of the gases supplied to the adsorption tower, the gas in a space that is not filled with the adsorbent inside the adsorption tower and the gas that has not been adsorbed on the adsorbent are first discharged preferentially from the adsorption tower. In this respect, since methane gas is supplied to the adsorption tower from its lower portion and offgas is released from the adsorption tower from its upper portion, the concentration of the methane adsorbed on the adsorbent in the adsorption tower increases toward the lower portion and decreases toward the upper portion. Therefore, when the inside of the adsorption tower is decompressed during the pressure equalization step to such an extent that the gas that has been already adsorbed on the adsorbent is released, the air included in the gases adsorbed on the adsorbent is preferentially released from the adsorbent due to the property of the adsorbent. Accordingly, in the initial pressure equalization (depressurizing) step, a gas having a particularly low methane content is discharged from the adsorption tower that has finished the adsorption step, and thereafter, a gas having a high methane concentration is gradually discharged.

That is, the gas released from the adsorption tower has a lower methane concentration in the earlier stage, and its concentration increases as the pressure equalization (depressurizing) step is repeated.

In addition, in the stage of performing the final pressure equalization (depressurizing) step after performing the pressure equalization (depressurizing) step, a gas having an even higher methane content is discharged due to the property of the adsorbent, and therefore, the purity of the methane adsorbed on the adsorbent in the adsorption tower is increased.

Further, when the gas is transferred from an adsorption tower that performs the pressure equalization (depressurizing) step to another adsorption tower that performs the pressure equalization (pressurizing) step, from the upper portion of the adsorption tower to the upper portion of the other, the concentration gradient of the methane adsorbed on the adsorbent in the adsorption tower is maintained in a state in which the methane concentration increases toward the upper portion and decreases toward the lower portion.

Accordingly, the recovery of a high-concentration methane gas is facilitated by performing the decompression step of recovering the methane gas from the lower portion of the adsorption tower after the pressure equalization (depressurizing) step.

In the pressure equalization (pressurizing) step, for example, in the initial pressure equalization (pressurizing) step, the adsorption tower receives the gas from another adsorption tower that is performing the final pressure equalization (depressurizing) step. Accordingly, the adsorption tower receives a gas having a higher methane concentration in initial runs of the pressure equalization (pressurizing) step performed in multiple stages, and the methane concentration of the gas received decreases each time the pressure equalization step is performed.

Then, since the gas is transferred from the upper portion of the adsorption tower to the upper portion of another adsorption tower, the gas that has increased the internal pressure of the adsorption tower tends to form a concentration gradient in which the methane concentration decreases toward the upper portion and increases toward the lower portion for the adsorbent in the adsorption tower.

Accordingly, by performing the pressurizing step after the pressure equalization (pressurizing) step and further starting the adsorption step, the methane concentration gradient in the adsorption tower cannot be easily collapsed, making it possible to recover the methane gas supplied into the adsorption tower such that the methane concentration increases toward the lower portion, and also to contribute to maintenance of a high concentration of the recovered methane gas.

Accordingly, concentrating methane gas by the above-described configuration has enabled the recovery of the methane gas with an even higher concentration.

In the case of performing the pressure equalization (depressurizing) step only once, the internal pressure of an adsorption tower after the pressure equalization (depressurizing) step only reaches substantially the median between the highest pressure and the lowest pressure of that adsorption tower. However, after the final pressure equalization (depressurizing) step performed after a plurality of runs of the pressure equalization step, the internal pressure of the adsorption tower can be further lowered as compared with substantially the median between the highest pressure and the lowest pressure of that adsorption tower.

Here, the highest pressure is the gas adsorption pressure during the adsorption step, and the lowest pressure is the gas desorption pressure during the decompression step. Each adsorbent has its unique characteristic values of the two pressures. Then, the power (differential pressure) required to desorb methane from the adsorbent during the decompression step corresponds to the pressure difference between a lower pressure after the final pressure equalization (depressurizing) step and the aforementioned lowest pressure.

This will be described using a specific example. In the case of performing the pressure equalization (depressurizing) step only once, the differential pressure that should be reduced in the decompression step is about ½ of the difference between the highest pressure and the lowest pressure. However, in the case of performing the initial pressure equalization (depressurizing) step and the final pressure equalization (depressurizing) step, the pressure equalization step is performed twice, and therefore, the differential pressure that should be reduced in the decompression step is about ⅓ of the difference between the highest pressure and the lowest pressure. In the case of further performing the pressure equalization step, the pressure equalization step is performed n times, and the differential pressure that should be reduced in the decompression step is about 1/(n+1) of the difference between the highest pressure and the lowest pressure.

That is, the more the number of times that the pressure equalization step is performed, the lower the load in performing the decompression step can be.

Note that an increase in the number of times of the pressure equalization step will result in an increased complexity of the steps and a longer total hour of the steps, and also reduce the effect of reducing the load in the decompression step by the increased number of times of the pressure equalization step. Accordingly, it is practical to perform the pressure equalization (depressurizing) step twice in the initial and final stages, or three times in the initial, middle, and final stages.

As a result, with the above-described methane gas concentration method, it is possible to decrease the differential pressure for each of the numbers of time of pressure equalization and reduce the load in performing the decompression step, while at the same time maintaining an appropriate methane gas concentration gradient in the adsorption tower, thus maintaining a high concentration of the recovered methane.

(Configuration 2)

Further, it is preferable that when the pressure equalization (depressurizing) step is composed of an initial pressure equalization (depressurizing) step and a final pressure equalization (depressurizing) step, and the pressure equalization (pressurizing) step is composed of an initial pressure equalization (pressurizing) step and a final pressure equalization (pressurizing) step, the gas discharged from the upper portion of one of the adsorption towers in the initial pressure equalization (depressurizing) step is supplied to the upper portion of another one of the adsorption towers that performs the final pressure equalization (pressurizing), and the gas discharged from the upper portion of one of the adsorption towers in the final pressure equalization (depressurizing) step is supplied to another one of the adsorption towers that performs the initial pressure equalization (pressurizing) step.

(Operation and Effect 2)

As a specific configuration for maintaining an appropriate methane gas concentration gradient in the adsorption tower, the gas is transferred from one of the adsorption towers that performs the pressure equalization (depressurizing) step to another one of the adsorption towers that performs the pressure equalization (pressurizing) step, from the upper portion of the one of the adsorption towers to the upper portion of the other one of the adsorption towers. In the case of performing each of the pressure equalization (depressurizing) step and the pressure equalization (pressurizing) step in two stages, it has been found that, when the gas discharged from the upper portion of the one of the adsorption towers in the initial pressure equalization (depressurizing) step is supplied to the upper portion of the other one of the adsorption towers that performs the final pressure equalization (pressurizing), and the gas discharged from the upper portion of one of the adsorption towers in the final pressure equalization (depressurizing) step is supplied to the other one of the adsorption towers that performs the initial pressure equalization (pressurizing) step, the methane gas concentration gradient in the adsorption tower can be appropriately managed without disruption. It has been also found by the experimental results described below that the above can improve the purity of the purified methane gas without significantly reducing the recovery rate.

That is, in the case of performing each of the pressure equalization (depressurizing) step and the pressure equalization (pressurizing) step in two stages, the gas transfer in both of the pressure equalization steps was found to show an improvement close to 10% in the methane gas purity in the product gas as compared with the case of using the lower portion of the adsorption tower. As a result of investigating different combinations, it has also been found that it is possible to obtain a product gas having a methane gas purity that is about 3% higher than that of an example having the second highest methane gas purity.

(Configuration 3)

Further, the methane-containing gas may be composed mainly of at least one gas selected from coal mine gas, biogas, reformed gas, and natural gas.

(Operation and Effect 3)

As used herein, coal mine gas is a gas generating from a coal mine, and about 20 to 40 Vol % of methane gas and about 60 to 80 Vol % of air (mainly containing nitrogen gas and oxygen gas) are contained in coal mine gas although this may vary depending on the conditions.

Biogas is, for example, a gas that has been generated by treating organic effluent or the like using a methane fermenter or the like and is composed mainly of methane gas and carbon dioxide, and contains about 40 to 60 Vol % of methane gas and about 20 to 50 Vol % of carbon dioxide although this may vary depending on the conditions.

Further, it is known that a methane-containing gas such as reformed gas or natural gas also contains about 4 to 95 Vol % of methane gas, and has been found to be suitably used for the methane gas concentration method according to the present invention.

(Configuration 4)

Further, it is possible to use, as the adsorbent, an adsorbent containing, as a main component thereof, at least one selected from the group consisting of activated carbon, zeolite, silica gel, and an organometallic complex having an average pore diameter of 4.5 to 15 Å as measured by the MP method and having a methane gas adsorption amount under atmospheric pressure and at 298 K of 20 Nml/g or more.

(Operation and Effect 4)

The use of such an adsorbent allows methane gas to be adsorbed on the methane gas adsorbent under atmospheric pressure and at 298 K.

That is, when the methane gas adsorption amount under atmospheric pressure and at 298 K is lower than 20 Nml/g, the concentration of the concentrated methane gas is reduced as a result of reduction in the methane gas adsorption performance at low pressures (in particular, approximately at atmospheric pressure). Also, an increased amount of the methane gas adsorbent is required to maintain the adsorption performance, leading to an increase in the size of the apparatus. Although the upper bound of the methane gas adsorption amount is not particularly limited, the currently attainable methane gas adsorption amount of a methane gas adsorbent is about 40 Nml/g or less. Further, when the average pore diameter measured by the MP method is smaller than 4.5 Å, the methane concentration in the concentrated coal mine gas is reduced as a result of an increase in the adsorption amounts of oxygen gas and nitrogen, or the adsorption rate becomes slower because the average pore diameter is close to the molecular diameter of the methane gas, thus reducing the methane gas adsorption performance or inhibiting the adsorption. On the other hand, when the average pore diameter measured by the MP method is larger than 15 Å, the concentration of the concentrated methane gas is reduced as a result of a reduction in the methane gas adsorption performance at low pressures (in particular, approximately at atmospheric pressure). In addition, an increased amount of the methane gas adsorbent is required to maintain the adsorption performance, leading to an increase in the size of the apparatus.

Effects of Invention

Accordingly, it has become possible to recover methane gas having a higher concentration, making it possible to effectively utilize coal mine gas, which has been difficult to reuse in the past.

BRIEF DESCRIPTION OF THE DRAWINGS

FIG. 12 is a diagram showing the transition of pressure in adsorption towers in the case of performing the method of FIG. 11.

BEST MODE FOR CARRYING OUT THE INVENTION

Hereinafter, a methane gas concentration method according to embodiments of the present invention will be described. Although a preferred example will be described below, the example is described for more specifically illustrating the present invention. Various modifications may be made without departing from the scope and sprit of the invention, and the present invention is not limited to the following description.

(Methane Concentration Apparatus)

Figure 1:
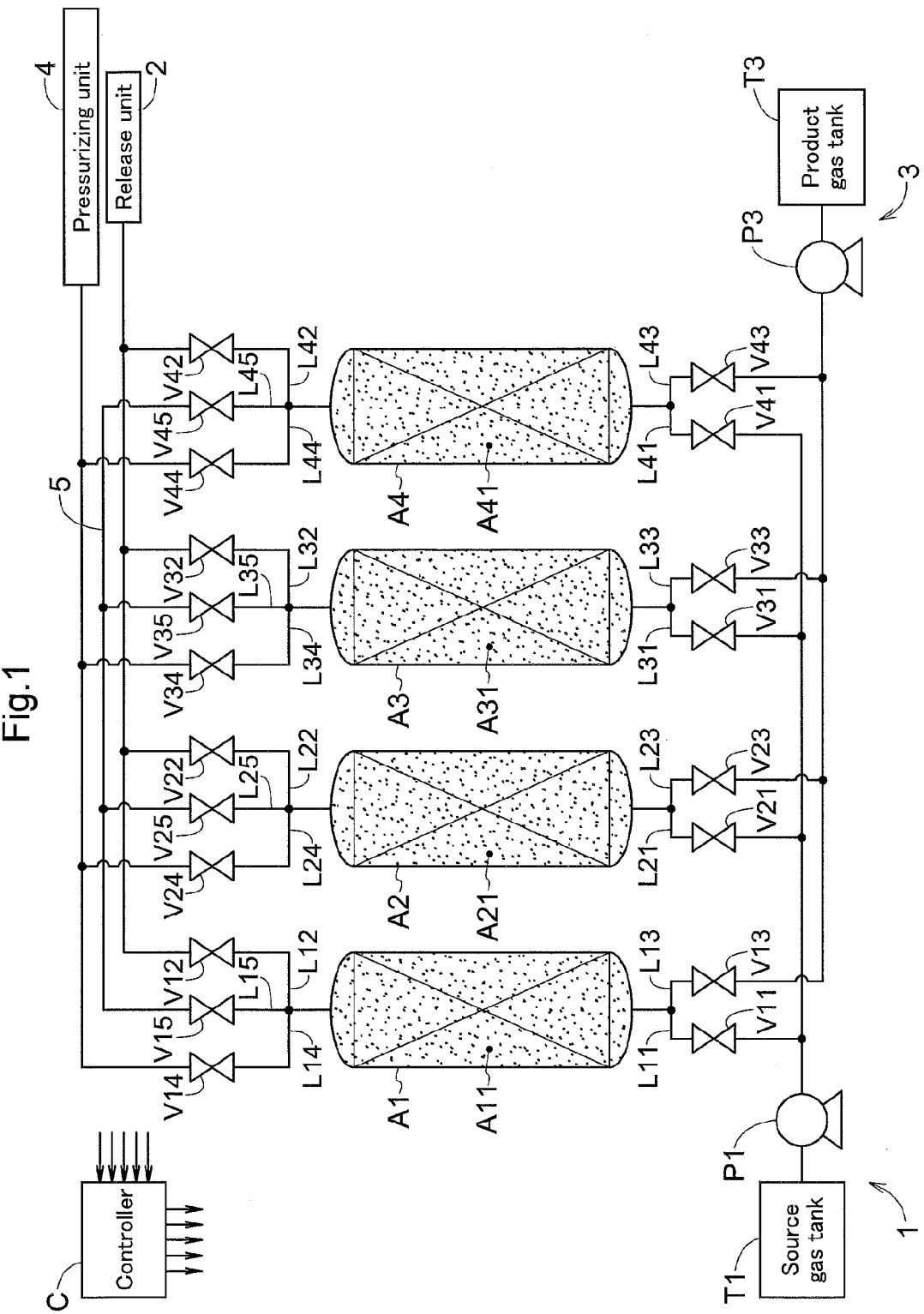
FIG. 1 is a schematic diagram of a methane concentration apparatus.

As shown in FIG. 1, a methane concentration apparatus is provided with adsorption towers A1 to A4 filled with adsorbents A11 to A41, a supply unit 1 and a release unit 2 for supplying coal mine gas from a source gas tank T1 and releasing exhaust gas, a recovery unit 3 for recovering the concentrated methane gas into a product gas tank T3, a controller C that controls the operations of the supply unit 1, the release unit 2, and the recovery unit 3.

Note that the adsorbents A11 to A41 are not particularly limited as long as they can selectively adsorb a flammable gas such as methane gas, but the use of a methane gas adsorbent 21a capable of selectively adsorbing methane gas under atmospheric pressure and at 298 K allows methane gas to be sufficiently adsorbed on the methane gas adsorbent 21a even under atmospheric pressure and at 298 K.

As the methane adsorbent 21, it is preferable to use a methane gas adsorbent 21a that is at least one selected from the group consisting of activated carbon, zeolite, silica gel, and an organometallic complex (e.g., copper fumarate, copper terephthalate, copper cyclohexane dicarboxylate) having an average pore diameter of 4.5 to 15 Å as measured by the MP method and having a methane gas adsorption amount under atmospheric pressure and at 298 K of 20 Nml/g or more. Note that the aforementioned average pore diameter is preferably 4.5 to 10 Å, more preferably, 5 to 9.5 Å, and the aforementioned methane gas adsorption amount is preferably 25 Nml/g or more.

Figure 4:
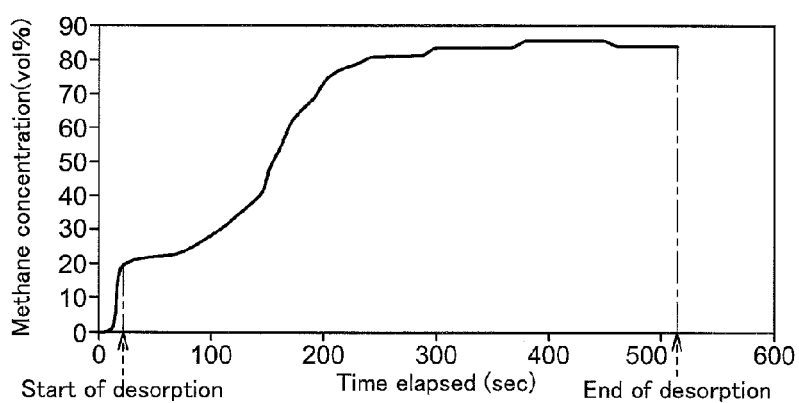
FIG. 4 is a graph showing methane adsorption properties of an adsorbent.

Specifically, this can be obtained, for example, by using, as a carbonaceous material, a carbide formed by completely carbonizing palm hush or palm hush charcoal in nitrogen gas at 600° C. and crushing the carbide to have a particle diameter of 1 to 3 mm, and activating the carbonaceous material under an atmosphere of 10 to 15 Vol % of water vapor, 15 to 20 Vol % of carbon dioxide, and nitrogen as the remainder at 860° C. using a batch-type flow activation oven having an inside diameter of 50 mm. Such an activated carbon has the property of selectively adsorbing methane gas contained in the air in a high pressure state near atmospheric pressure and desorbing the adsorbed methane gas in a decompressed state lower than the low pressure state that is lower than atmospheric pressure, and also has the property of preferentially desorbing the air when desorbing methane gas, and has adsorption properties as shown in FIG. 4.

(Adsorption Towers)

The adsorption towers A1 to A4 are filled with adsorbents A11 to A41, respectively. Also, supply lines L11 to L41 for supplying coal mine gas from the source gas tank T1 by a supply pump P1 are provided below the adsorption towers A1 to A4 to form a supply unit 1, and release lines L12 to L42 for releasing, of the coal mine gas supplied to the adsorption towers A1 to A4, exhaust gas having a very low methane concentration and being composed mainly of nitrogen gas and oxygen gas are provided above the adsorption towers A1 to A4 to form a release unit 2. The coal mine gas is supplied from the supply unit 1 to the adsorption towers A1 to A4, and the exhaust gas that has not been adsorbed on the adsorbents A11 to A41 is discharged from the release unit 2, thereby providing a configuration that allows the methane gas to be adsorbed on the adsorbents A11 to A41 and be separated from the exhaust gas. Further, for the adsorption towers A1 to A4, recovery lines L13 to L43 for recovering the methane gas adsorbed on the adsorbents A11 to A41 are provided below the adsorption towers A1 to A4 to form the recovery unit 3, thus providing a configuration that enables collection of, from the coal mine gas supplied from the supply unit 1, a high-concentration methane gas that has been adsorbed on the adsorbents A11 to A41 and concentrated. The recovery unit 3 is provided with a vacuum pump P3 for collecting the high-concentration methane gas from the adsorption towers A1 to A4 into the product gas tank T3 via the recovery lines L13 to L43.

Pressurizing lines L14 to L44 for supplying a pressurizing air to the adsorption towers A1 to A4 are connected to the upper portions of the adsorption towers A1 to A4 to form a pressurizing unit 4. Furthermore, pressure equalization lines L15 to L45 for providing connection between the adsorption towers A1 to A4 are connected to the upper portions of the adsorption towers A1 to A4 to form a pressure equalization unit 5 for transferring the gas inside each of the adsorption towers A1 to A4 to another one of the adsorption towers A1 to A4, from the upper portion of the adsorption tower (A1 to A4) to the upper portion of the other one of the adsorption towers A1 to A4.

Note that switching valves V11 to V45 are provided in the gas lines L11 to L45, thus providing a configuration that enables the controller C to perform overall control of the switching between supply, discharge, and suspension of the gas to the adsorption towers A1 to A4 by the operation of the pumps P1 and P3.

(Methane Gas Concentration Method)

Figure 2:
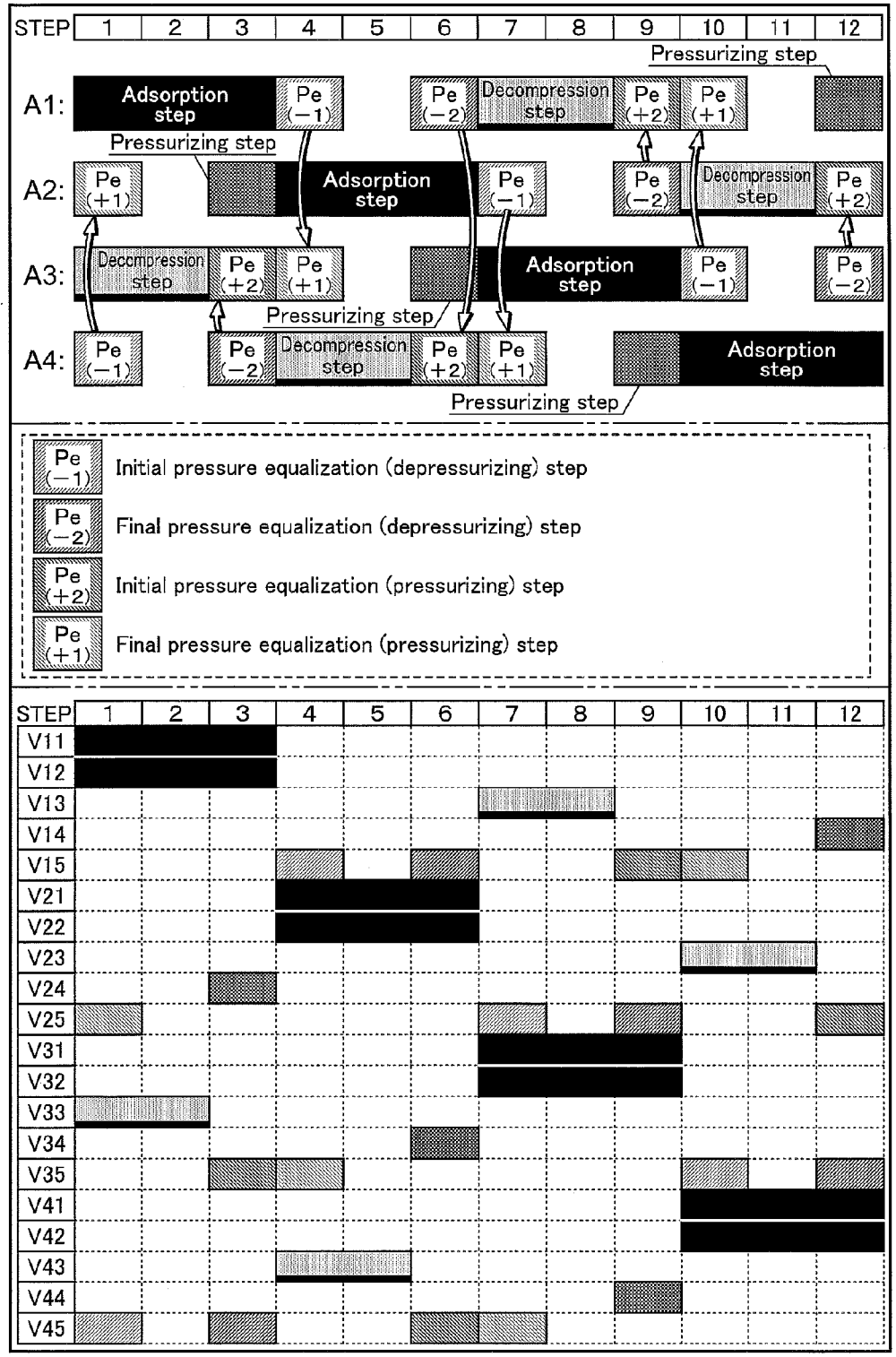
FIG. 2 is a diagram showing the operation of a methane concentration apparatus that corresponds to a methane concentration method.

As shown in FIG. 2, the controller C controls the switching valves V11 to V45 and the pumps P1 and P3 to control the operation so as to perform, in the adsorption towers A1 to A4, in order:

an adsorption step of receiving supply of methane gas in a high pressure state near atmospheric pressure from the lower portion of the adsorption towers A1 to A4, adsorbing the methane gas on the adsorbents A11 to A41, and releasing offgas composed mainly of air from the upper portions of the adsorption towers A1 to A4;

an initial pressure equalization (depressurizing) step of transferring a gas having a relatively low methane concentration in one of the adsorption towers A1 to A4 that is in a high pressure state to another one of the adsorption towers A1 to A4 that is in an intermediate pressure state at a pressure lower than that of the one of the adsorption towers A1 to A4 so as to bring the pressure in the one of the adsorption towers A1 to A4 into a high pressure-side intermediate pressure state;

a standby step;

a final pressure equalization (depressurizing) step of transferring a gas in which the methane concentration has been slightly increased than that in the initial pressure equalization (depressurizing) step in one of the adsorption towers A1 to A4 that is in the high pressure-side intermediate pressure state at a pressure higher than that of the low pressure state to another one of the adsorption towers A1 to A4 that is in a low pressure state so as to bring the pressure in the one of the adsorption towers A1 to A4 into a low pressure-side intermediate pressure state;

a decompression step of, after the internal pressure of the tower has been reduced by the pressure equalization (depressurizing) step, further decompressing the one of the adsorbents A11 to A41 into a low pressure state to desorb the methane gas adsorbed on the one of the adsorbents A11 to A41 and recovering the methane gas from the lower portion of the one of the adsorption towers A1 to A4;

an initial pressure equalization (pressurizing) step of receiving, into the one of the adsorption towers A1 to A4 that is in the low pressure state, the gas in the other one of the adsorption towers A1 to A4 that is in the high pressure-side intermediate pressure state so as to bring the pressure in the one of the adsorption towers A1 to A4 into the low pressure-side intermediate pressure state;

a final pressure equalization (pressurizing) step of receiving, into the one of the adsorption towers A1 to A4 that is in the low pressure-side intermediate pressure state, the gas in another one of the adsorption towers A1 to A4 that is in the high pressure state so as to bring the pressure in the one of the adsorption towers A1 to A4 into the high pressure-side intermediate pressure state;

the standby step; and a pressurizing step of, after the internal pressure of the tower has been increased by the pressure equalization (pressurizing) step, further supplying a pressurizing air into the one of the adsorption towers A1 to A4 from the upper portion of another one of the adsorption towers A1 to A4 so as to restore the corresponding one of the adsorbents A11 to A41 into the high pressure state capable of selectively adsorbing the methane gas.

Figure 3:
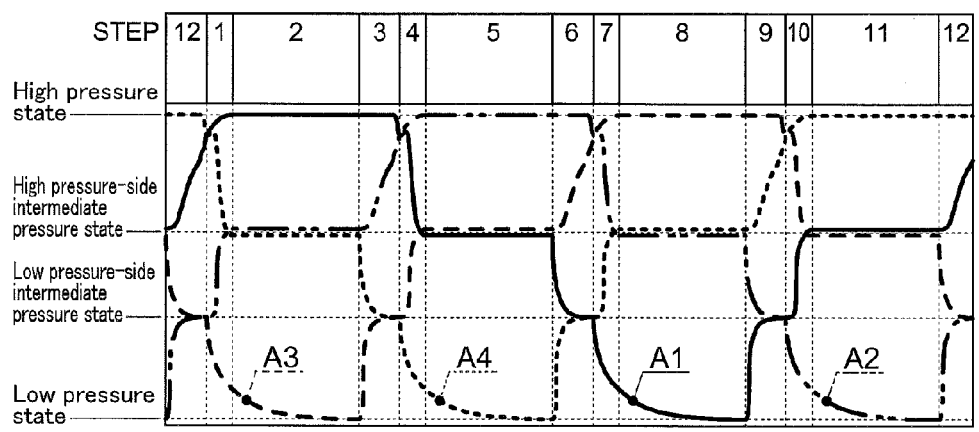
FIG. 3 is a diagram showing the transition of pressure in adsorption towers in the case of performing the method of FIG. 2.

By such a control, the changes in the internal pressures of the adsorption towers A1 to A4 transition as shown in FIG. 3.

Specifically, the adsorption tower A1 is controlled in the following manner. Although the same operation will also be performed for the other adsorption towers A2 to A4 in a phase shifted manner, the detailed description thereof has been omitted and replaced by the description with reference to FIG. 2 to avoid redundancy. Note that the adsorption towers A1 to A4 are hereinafter referred to as first to fourth adsorption towers A1 to A4 in this order. Further, FIG. 2 summarizes the open/close states of the open/close valves and the like in the steps in association with each other. Note that in FIG. 2, the upper part of the drawing sequentially shows the details of the steps and the lower part of the drawing shows the state of switching of the piping channels in the steps. Further, the open state of the open/close valve and the like used in each of the steps is indicated by the same hatching as that in the corresponding step in the upper part of the drawing.

<1 to 3> Adsorption Step

Coal mine gas is introduced from the source gas tank T1 to the first adsorption tower A1. At this time, the pressure in the first adsorption tower A1 is substantially atmospheric pressure as shown in FIG. 3, and is maintained in a high pressure state near atmospheric pressure that has been increased by the supply pressure of the supply pump P1, and the methane gas contained in the coal mine gas supplied from the source gas tank T1 via the switching valve V11 of the supply line L11 is adsorbed on the adsorbent A11, while the remaining exhaust gas is being discharged via the switching valve V12 of the release line L12.

Note that at this time, as shown in FIG. 2, the second adsorption tower A2 performs <1> a final pressure equalization (pressurizing) step, and transitions to <3> a pressurizing step, with <2> a standby state in between.

Also, the third adsorption tower A3 performs an initial pressure equalization (pressurizing) step, following a decompression step.

Furthermore, the fourth adsorption tower A4 performs an initial pressure equalization (depressurizing) step, and transitions to a final pressure equalization (depressurizing) step, with the standby step in between.

<4> Initial Pressure Equalization (Depressurizing) Step

The first adsorption tower A1 that has finished the adsorption step performs an initial pressure equalization (depressurizing) step between itself and the third adsorption tower A3 that performs the final pressure equalization (pressurizing) step. That is, non-adsorbed gas in the tower is discharged via the switching valve V15 of the pressure equalization line L15, and is transferred to the third adsorption tower A3 via the switching valve V35 of the pressure equalization line L35. Consequently, pressure equalization is performed between the first adsorption tower A1 and the third adsorption tower A3 in the low pressure-side intermediate pressure state, and the first adsorption tower A1 transitions to the high pressure-side intermediate pressure state, as shown in FIG. 3.

Note that at this time, through the operation of the open/close valves and the like as shown in FIG. 2, the second adsorption tower A2 performs the adsorption step and the fourth adsorption tower A4 performs the decompression step.

<5> Standby Step

Next, the first adsorption tower A1 enters the standby state, and the high pressure-side intermediate pressure state is maintained, while keeping a balance in time with the adsorption step, which requires the longest time. At this time, the second adsorption tower A2 performs the adsorption step, the third adsorption tower A3 is also in the standby step, and the fourth adsorption tower A4 continues the decompression step.

<6> Final Pressure Equalization (Depressurizing) Step

Next, the first adsorption tower A1 performs a final pressure equalization (depressurizing) step between itself and the fourth adsorption tower A4 that has finished the decompression step and performs the initial pressure equalization (pressurizing) step. That is, any non-adsorbed gas in the tower and the initially desorbed gas composed mainly of the air from the adsorbent A11 are discharged via the switching valve V15 of the pressure equalization line L15, and are transferred to the fourth adsorption tower A4 via the switching valve V45 of the pressure equalization line L45. Consequently, as shown in FIG. 3, pressure equalization is performed between the first adsorption tower A1 and the fourth adsorption tower A4 that has finished the decompression step and is in the low pressure state, and the first adsorption tower A1 transitions to the low pressure-side intermediate pressure state.

Note that at this time, through the operation of the open/close valves and the like as shown in FIG. 2, the second adsorption tower A2 performs the adsorption step and the third adsorption tower A3 performs the pressurizing step.

<7 to 8> Decompression Step

The first adsorption tower A1 that has reached the low pressure-side intermediate pressure state is in a state in which a high-concentration methane gas is adsorbed on the adsorbent A11 in the tower, and the high-concentration methane gas adsorbed on the adsorbent A11 is recovered by performing a decompression step of decompressing the inside of the tower from the low pressure-side intermediate pressure state to the low pressure state. That is, the concentrated methane gas is recovered into the product gas tank T3 via the switching valve V13 of the recovery line L13 by the power of the vacuum pump P3. Consequently, as shown in FIG. 3, the first adsorption tower A1 transitions from the low pressure-side intermediate pressure state to the low pressure state.

The load of the vacuum pump P3 at this time corresponds to the differential pressure from the low pressure-side intermediate pressure state to the low pressure state, and is thus lower than that has been required to reduce the pressure from the intermediate pressure to the low pressure state in the past.

Note that at this time, through the operation of the open/close valves and the like as shown in FIG. 2, the second adsorption tower A2 performs <7> the initial pressure equalization (depressurizing) step between itself and the fourth adsorption tower A4, and then enters <8> the standby step.

Also, the adsorption step proceeds in the third adsorption tower A3.

Furthermore, the fourth adsorption tower A4 performs <7> the final pressure equalization (pressurizing) step, and then transitions to <8> the standby step.

<9> Initial Pressure Equalization (Pressurizing) Step

The first adsorption tower A1, which has entered the low pressure state and has released the adsorbed methane gas and in which the adsorbent A11 has been regenerated, performs an initial pressure equalization (pressurizing) step between itself and the second adsorption tower A2, thereby restoring the pressure in the tower and receiving the exhaust gas that has been discharged in the final pressure equalization (depressurizing) step in the second adsorption tower A2 and in which the methane concentration has been increased by the initially desorbed gas from the adsorbent A21. That is, the gas in the tower discharged from the second adsorption tower A2 in the high pressure-side intermediate pressure state is received in the pressure equalization lines L15 to L25 via the switching valves V15 and V25. Consequently, as shown in FIG. 3, the first adsorption tower A1 restores its pressure from the low pressure state to the low pressure-side intermediate pressure state.

Note that at this time, through the operation of the open/close valves and the like as shown in FIG. 2, the third adsorption tower A3 continues the adsorption step and the fourth adsorption tower A4 performs the pressurizing step.

<10> Final Pressure Equalization (Pressurizing) Step

The first adsorption tower A1 that has restored its pressure to the low pressure-side intermediate pressure state attempts to further restore the pressure in the tower by subsequently performing a final pressure equalization (pressurizing) step between itself and the third adsorption tower A3 that performs the adsorption step immediately after finishing the initial pressure equalization (depressurizing) step. That is, the gas in the tower discharged from the third adsorption tower A3 in the high pressure state is received in the pressure equalization lines L15 to L35 via the switching valves V15 and V35. Consequently, as shown in FIG. 3, the first adsorption tower A1 restores its pressure from the low pressure-side intermediate pressure state to the high pressure-side intermediate pressure state.

Note that at this time, through the operation of the open/close valves and the like as shown in FIG. 2, the second adsorption tower A2 performs the decompression step and the fourth adsorption tower A4 performs the adsorption step.

<11> Standby Step

Next, the first adsorption tower A1 enters the standby state, and the high pressure-side intermediate pressure state is maintained, while keeping a balance in time with the adsorption step, which requires the longest time. At this time, the second adsorption tower A2 performs the decompression step, the third adsorption tower A3 is also in the standby step, and the fourth adsorption tower A4 continues the adsorption step.

<12> Pressurizing Step

The pressure of the first adsorption tower A1 that has restored its pressure to the high pressure-side intermediate pressure state is restored to the high pressure state near atmospheric pressure by injection of the air. That is, the atmospheric air is flowed into the first adsorption tower A1 via the switching valve V14 from the pressurizing line L14. Consequently, the inside of the first adsorption tower A1 is restored to the high pressure state near atmospheric pressure, and is regenerated into a state capable of adsorbing the methane gas contained in the coal mine gas by supply of coal mine gas.

Note that at this time, through the operation of the open/close valves and the like as shown in FIG. 2, the second adsorption tower A2 performs the initial pressure equalization (pressurizing) step, the third adsorption tower A3 performs the final pressure equalization (depressurizing) step, i.e., they perform pressure equalization with each other. Further, the fourth adsorption tower A4 performs the adsorption step.

<Transition of Methane Gas Concentration Distribution in Adsorption Tower>

Figure 5:
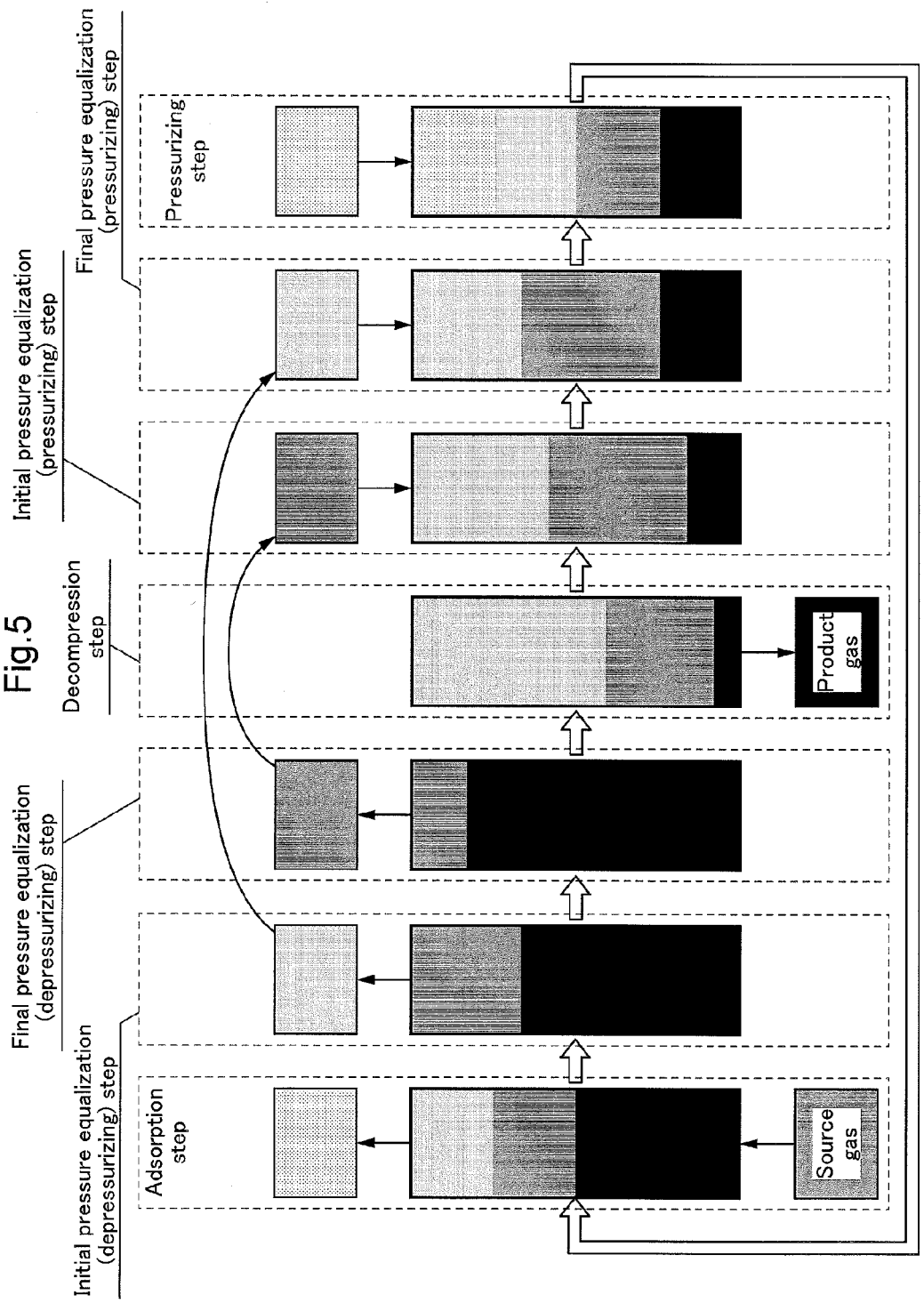
FIG. 5 is a graph showing the transition of a concentration distribution of methane adsorbed in the adsorption tower.

It seems that the methane gas concentration distribution in the first adsorption tower A1 during the above-described steps proceeds as shown in FIG. 5.

That is, when a coal mine gas having a moderate methane concentration is supplied to the adsorption tower in the adsorption step, an exhaust gas containing substantially no methane gas is discharged, and as a result, the methane concentration in the tower is increased.

The adsorption step ends when the methane concentration in the discharged exhaust gas reaches a certain threshold, and the method proceeds to the initial pressure equalization (depressurizing) step. In this state, there is no gas supplied into the first adsorption tower A1, and only gas movement caused by expansion, diffusion, and the initially desorbed gas of the gas adsorbed on the adsorbent A11 occur in the tower. Then, a gas composed mainly of non-adsorbed gas remaining in the header space or the like in the first adsorption tower A1 and containing a relatively low concentration methane is discharged from the upper portion of the first adsorption tower A1 to the outside of the first adsorption tower A1.

Thereafter, in the stage in which the final pressure equalization step is performed through the standby step, a medium-concentration methane-containing gas having a relatively high methane gas concentration and containing the initially desorbed gas desorbed from the adsorbent A11 in the first adsorption tower A1 is discharged to the outside of the first adsorption tower A1. Then, at this point, a high-methane concentration region is formed over a wide range in the lower portion of the first adsorption tower A1, and the gas containing a medium-concentration methane is retained in the upper portion thereof.

When the decompression step is performed in this state, the high-concentration methane gas can be collected from the lower portion of the first adsorption tower A1. While methane gas is recovered over a predetermined concentration range, methane is adsorbed on the adsorbent A11 in the first adsorption tower A1 in a concentration distribution in which the methane gas concentration increases toward the lower portion.

When the initial pressure equalization (pressurizing) step is performed after the decompression step, the gas containing a medium-concentration methane flows into the first adsorption tower A1. This gas moves downward while being adsorbed on the adsorbent A11. Basically, a medium-concentration methane gas tends to be adsorbed on the adsorbent A11 in the upper portion of the first adsorption tower A1 because the lower portion of the first adsorption tower A1 is in the sealed state, but the gas has a strong tendency to flow in so as to be diffused and adsorbed throughout the inside of the tower, and to be filled so as to increase the overall methane concentration in the inside of the first adsorption tower A1. Therefore, the state in which methane is adsorbed on the adsorbent A11 in the concentration distribution in which the methane gas concentration increases toward the lower portion of the first adsorption tower A1 is maintained, and the concentration difference between the upper portion and the lower portion of the first adsorption tower A1 is reduced by an amount due to the diffusion velocity of the gas containing a medium-concentration methane.

When the final pressure equalization (pressurizing) step is further performed, a gas containing a low-concentration methane flows into the first adsorption tower A1. Then, the overall concentration distribution in the tower is maintained in the concentration distribution in which the methane gas concentration increases toward the lower portion of the first adsorption tower A1, while uneven concentration distribution in the upper portion of the tower is being defused. Likewise, when the pressurizing step is further performed, an air free of methane is supplied from the upper portion, and therefore, the concentration distribution in which the methane gas concentration increases toward the lower portion of the first adsorption tower A1 is maintained.

Further, the lower the tower internal pressure, the slower the diffusion velocity of the gas introduced into the first adsorption tower A1 in the first adsorption tower A1. Accordingly, a gas or air having a lower methane concentration is more likely to remain in the upper portion of the tower, and therefore, it can also be considered that the concentration distribution in which the methane gas concentration increases toward the lower portion of the first adsorption tower A1 tends to have a steep gradient when the pressure equalization (pressurizing) step is performed in a divided manner for a larger number of times.

Accordingly, in the pressure equalization (depressurizing) step, the gas is successively discharged from the inside of the tower such that the methane concentration gradually increases. Conversely, in the pressure equalization (pressurizing) step, the gas is successively introduced into the tower such that the methane concentration gradually decreases. Therefore, the methane gas recovered in the decompression step is always recovered from the region having the highest methane concentration in the tower, thus making it possible to increase the concentration of the recovered methane gas.

EXAMPLE

The following four adsorption towers were provided, and the following adsorbents A11 to A41 were filled therein. The adsorption towers were connected by piping as shown in FIG. 1, thus providing a methane concentration apparatus. To this methane concentration apparatus, a simulated coal mine gas was supplied at 17 L/min, and the methane gas concentration operation shown in FIGS. 2 and 3 was performed under the following operating conditions.

Adsorption tower: Cylindrical (inside diameter: 54 mm, volume: 4.597 L)
: Four towers
Adsorbent: Activated carbon
Obtained by using, as a carbonaceous material, a carbide formed by completely carbonizing palm hush or palm hush charcoal in nitrogen gas at 600° C. and crushing the carbide to have a particle diameter of 1 to 3 mm, and activating the carbonaceous material under an atmosphere of 10 to 15 Vol % of water vapor, 15 to 20 Vol % of carbon dioxide, and nitrogen as the remainder at 860° C. using a batch-type flow activation oven having an inside diameter of 50 mm.
Pore diameter: 8.5 Å (average pore diameter as measured by the MP method)
Pore volume: 0.45 ml/g (volume as measured by the HK method)
Ratio of the volume of pores having an average pore diameter of 10 Å or less to the total pore volume: 83% (the nitrogen adsorption amount ratio under a relative pressure of 0.013 or less was the same)
Specific surface area: 1025 m$^2$/g (specific surface area as measured by the BET method)
Methane gas adsorption capacity at atmospheric pressure and 298 K: 27 NmL/g
Simulated coal mine gas: Methane 20%
: Nitrogen 80%
Operating conditions
Flow velocity: 17 L/min
Gas adsorption pressure (gauge pressure): 14 kPa
Gas desorption pressure (gauge pressure): −99 kPa
Condition of ending the adsorption step: until the methane concentration in the exhaust gas reached 3 vol % (144 seconds)
As a result, a methane gas having a methane concentration of 57.1 vol % was obtained at 5.1 L/min as a product gas.

Comparative Example 1

Comparison with Three-Tower PSA

Figure 6:
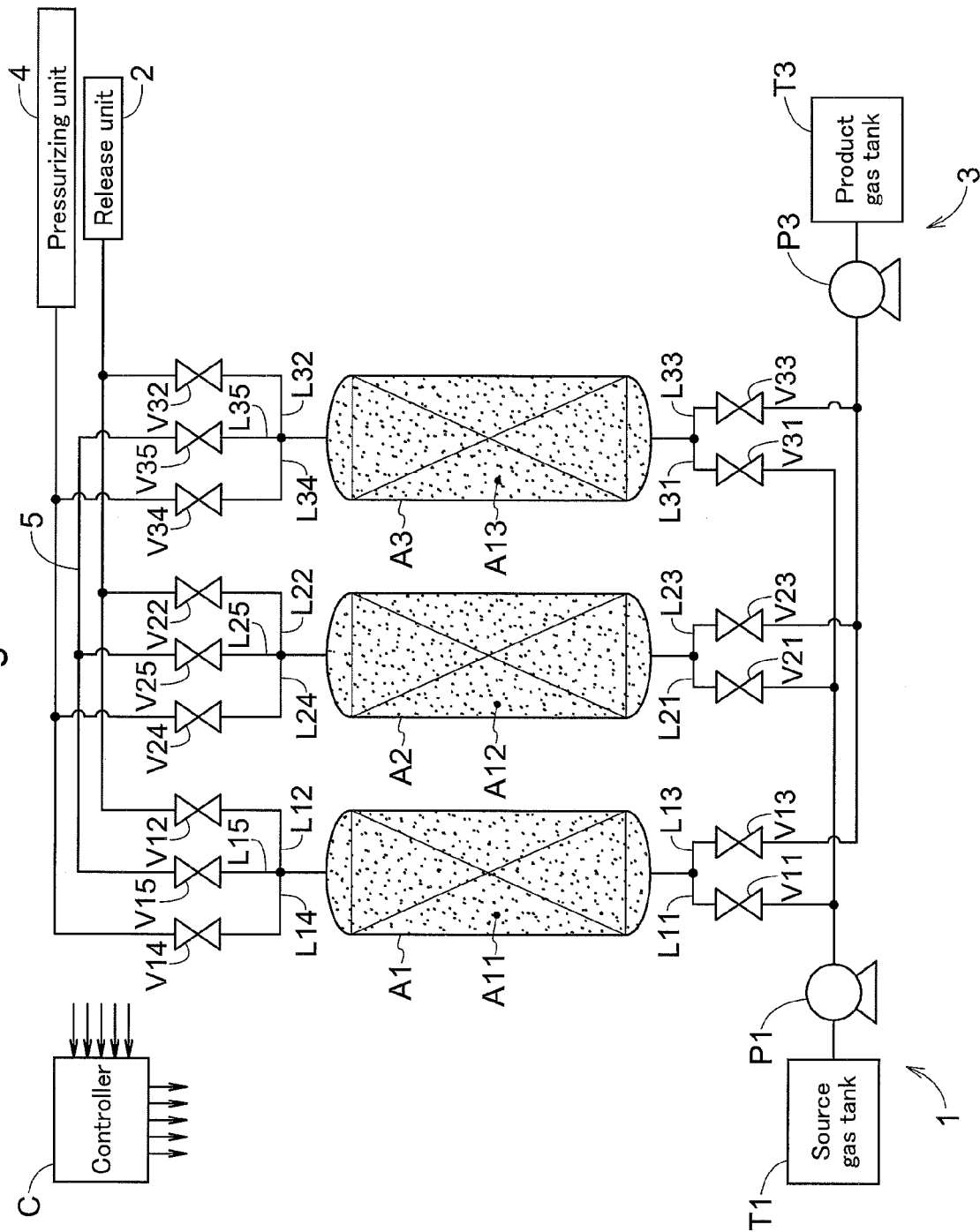
FIG. 6 is a schematic diagram of a conventional methane concentration apparatus including three adsorption towers.
Figure 7:
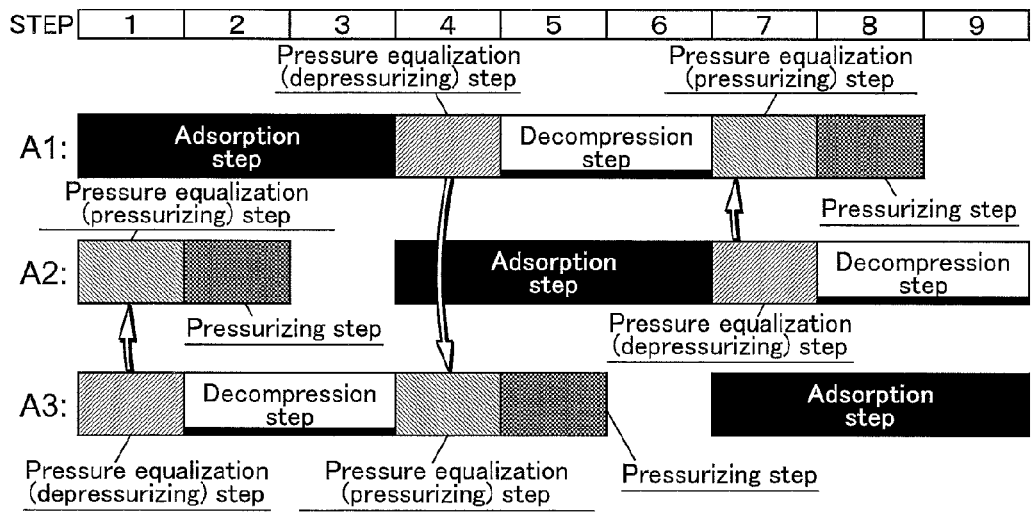
FIG. 7 is a diagram showing a methane concentration method performed by the conventional methane concentration apparatus including three adsorption towers.
Figure 8:
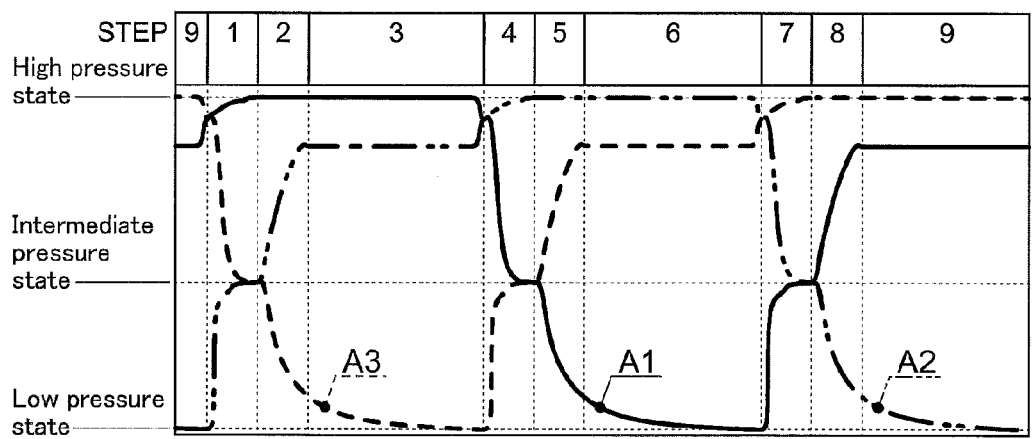
FIG. 8 is a diagram showing the transition of pressure in adsorption towers in the case of performing the method of FIG. 7.

To evaluate the performance of the methane concentration apparatus of the present invention, the methane gas concentration operation was performed using a conventional PSA apparatus. Specifically, the following three adsorption towers A1 to A3 were provided, and the following adsorbents A11 to A31 were filled therein. The adsorption towers A1 to A3 were connected by piping as shown in FIG. 6, thus providing a methane concentration apparatus. To this methane concentration apparatus, a simulated coal mine gas was supplied at 17 L/min, and the methane gas concentration operation shown in FIGS. 7 and 8 was performed under the following operating conditions. Note that in FIGS. 6 to 8, the same configurations as those of the previous embodiment (FIGS. 1 to 3) are denoted by the same reference numerals and names, and the description thereof has been omitted.
Adsorption tower: Cylindrical (inside diameter: 54 mm, volume: 4.597 L)
: Three towers
Adsorbent: Activated carbon (the same as Example)
Simulated coal mine gas: Methane 20%
: Nitrogen 80% (the same as Example)
Operating conditions
Flow velocity: 17 L/min
Gas adsorption pressure (gauge pressure): 14 kPa
Gas desorption pressure (gauge pressure): −99 kPa
Condition of ending the adsorption step: until the methane concentration in the exhaust gas reached 3 vol % (179 seconds)
(the same as Example)
As a result, a methane gas having a methane concentration of 54.1 vol % was obtained at 5.4 L/min as a product gas.

A comparison between these results showed that performing the methane concentration method according to the present invention as described in Example shortened the time required to end the adsorption step, but the methane gas concentration of the obtained product gas was increased by about 3%, making it possible to concentrate methane gas with a high concentration.
Further, it was found that whereas the load of the vacuum pump was 67 kPa in Comparative Example 1, the methane gas was desorbed with a load of about 38 kPa in Example, and the flow rate of the obtained product gas did not significantly change, making it possible to significantly reduce the power required for the methane concentration operation.

Comparative Example 2

Figure 9:
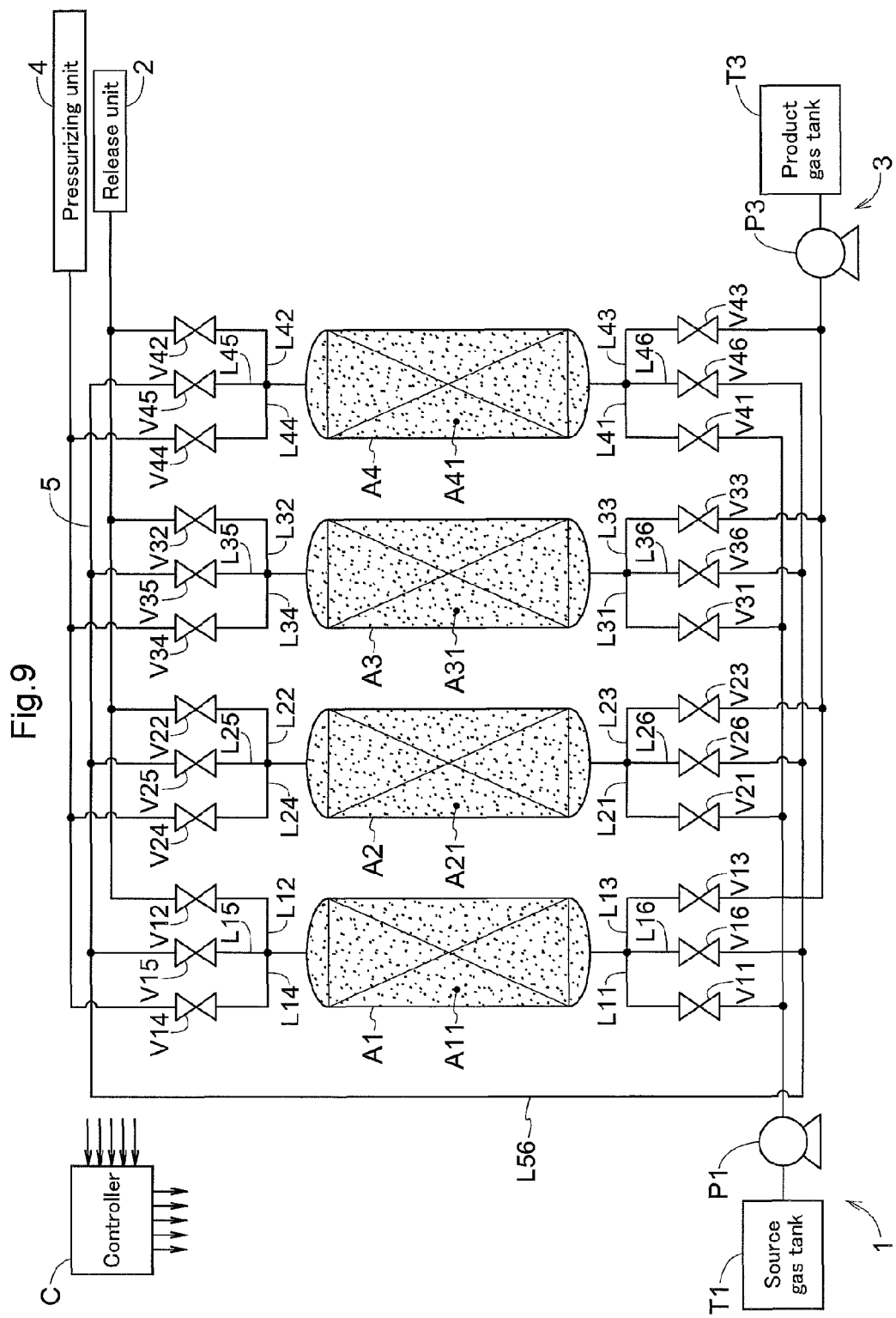
FIG. 9 is a schematic diagram of a methane concentration apparatus including a lower pressure equalization line.

Influence by the Connection Mode of the Pressure Equalization Lines in the Pressure Equalization Step In performing the above-described methane gas concentration method, the pressure equalization operations were performed in the upper portions of the adsorption towers, and the influence on the methane concentrating effect by the paths along which the pressure equalization operations were performed was examined.
Specifically, a methane concentration apparatus was formed in the same manner as that of Example (FIG. 1) except that the pressure equalization unit 5 was formed by providing lower pressure equalization lines L16 to L46 including switching valves V16 to V46 below the adsorption towers A1 to A4, and providing a transportation line L56 for connecting the pressure equalization lines L15 to L45 and the lower pressure equalization lines L16 to L46, as shown in FIG. 9. The methane concentration apparatus was configured such that the gas inside the tower can be transported from both the upper and lower sides of any of the adsorption towers A1 to A4 to both the upper and lower sides of another one of the adsorption towers A1 to A4 by controlling switching of the switching valves V11 to V46.
Table 1 shows the results of comparing the product gas concentrations obtained with such a configuration by variously changing the transfer mode for transferring a gas from an adsorption tower that performs the pressure equalization (depressurizing) step to another adsorption tower that performs the pressure equalization (pressurizing) step.

TABLE 1

| | | | |
|---|---|---|---|
| Final pressure equalization (depressurizing) step → Initial pressure equalization (pressurizing) step | Low → Low | Up → Low | Up → Up |
| Initial pressure equalization (depressurizing) step → Final pressure equalization (pressurizing) step | Low → Low | Up → Up | Up → Up |
| Methane gas concentration in product gas (vol %) | 47.9 | 54.1 | 57.1 |
| Adsorption time (sec) | 123 | 148 | 144 |
| Recovery rate (%) | 92.9 | 92 | 90 |

From Table 1, it has been found that in the case of performing the above-described methane gas concentration method, the mode in which the tower gas is transported from the upper portion to the upper portion is particularly preferable as the transfer mode for transferring a gas from an adsorption tower that performs the pressure equalization (depressurizing) step to another adsorption tower that performs the pressure equalization (pressurizing) step.

That is, in the case of performing each of the pressure equalization (depressurizing) step and the pressure equalization (pressurizing) step in two stages, nearly 10% improvement in the methane gas purity in the product gas was observed as compared with when the lower portion of the adsorption tower was used in the gas transfer in any of the pressure equalization steps. Different combinations were also investigated, and the example showing the second highest methane gas purity was the case described in Patent Document 2 in which the gas transfer is performed from the upper portion of the adsorption tower that performs the final pressure equalization (depressurizing) step to the lower portion of the adsorption tower that performs the initial pressure equalization (pressurizing) step, and the gas transfer is performed from the upper portion of the adsorption tower that performs the initial pressure equalization (depressurizing) step to the upper portion of the adsorption tower that performs the final pressure equalization (pressurizing) step. It has been found that, as compared with this case as well, a product gas having a methane gas purity that is about 3% higher was obtainable.

Other Embodiments

Although the pressurizing step was performed up to atmospheric pressure in the previous embodiment, the provision of a blower or a pump in the pressurizing lines is advantageous where it is necessary to increase the internal pressure of the tower to a value slightly higher than atmospheric pressure because it can improve the operation efficiency.

Although the exhaust gas discharged from the release unit 2 is directly released into the atmosphere in the previous embodiment, it is possible to provide an offgas tank in the release lines and temporarily stores the exhaust gas therein. This exhaust gas can also be used as the pressurizing air.

The adsorbents that adsorb methane are not limited to those described above. Any adsorbent can be effectively used as long as it has the property of selectively adsorbing methane gas contained in air in a high pressure state and desorbing the adsorbed methane gas in a low pressure state, and also has the property of preferentially desorbing the air when desorbing the methane gas as shown in FIG. 4, and any of various known adsorbents is applicable.

However, it is evident that the above-described activated carbon having an average pore diameter of 4.5 to 15 Å as measured by the MP method and having a methane gas adsorption amount under atmospheric pressure and at 298 K of 20 Nml/g or more has a particularly high degree of effectiveness in performing the above-described methane gas concentration method.

Although the above-described embodiment shows an example in which four adsorption towers are used, the same methane gas concentration method can also be performed when five or more adsorption towers are used.

Figure 10:
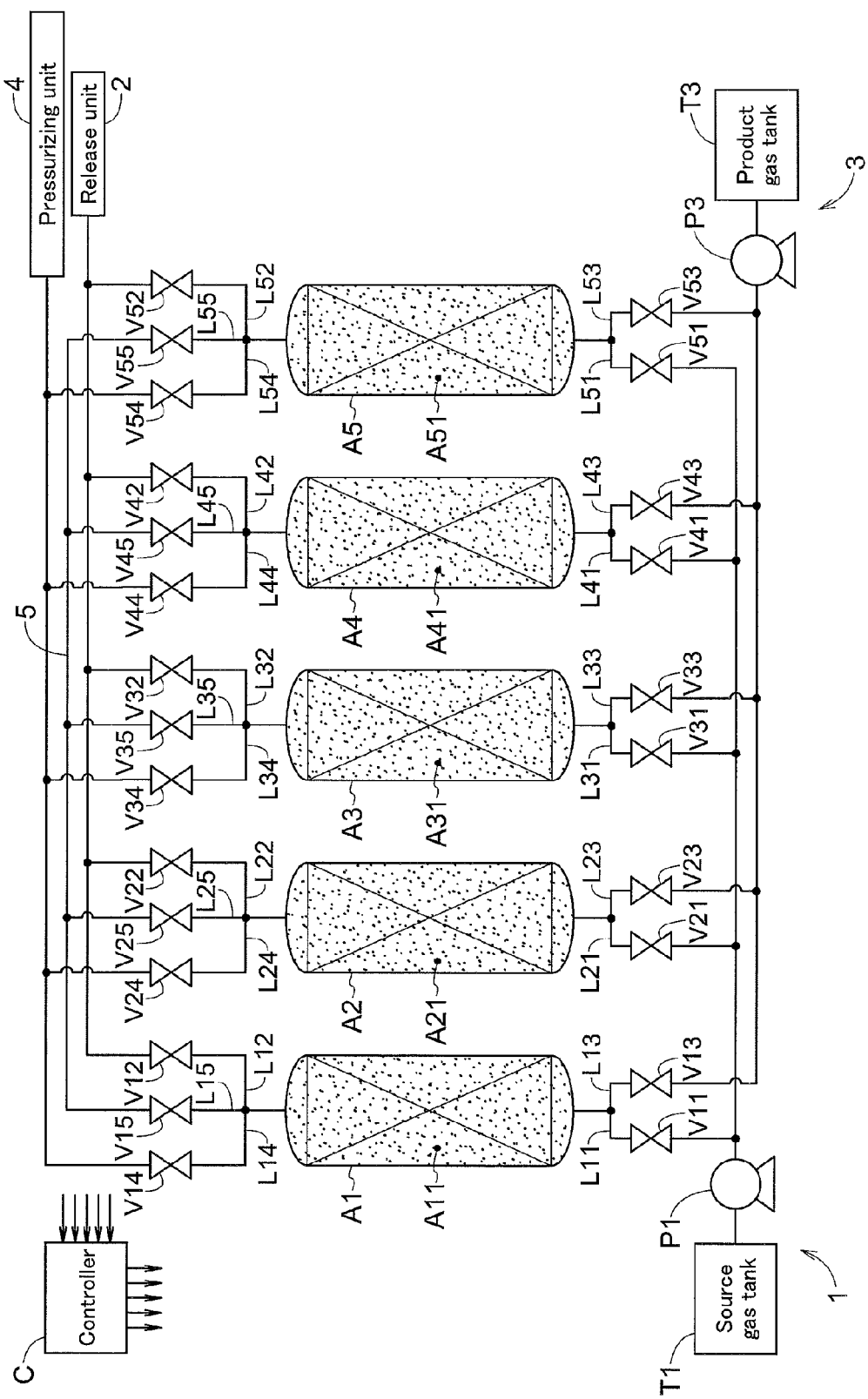
FIG. 10 is a schematic diagram of a methane concentration apparatus including five adsorption towers.
Figure 11:
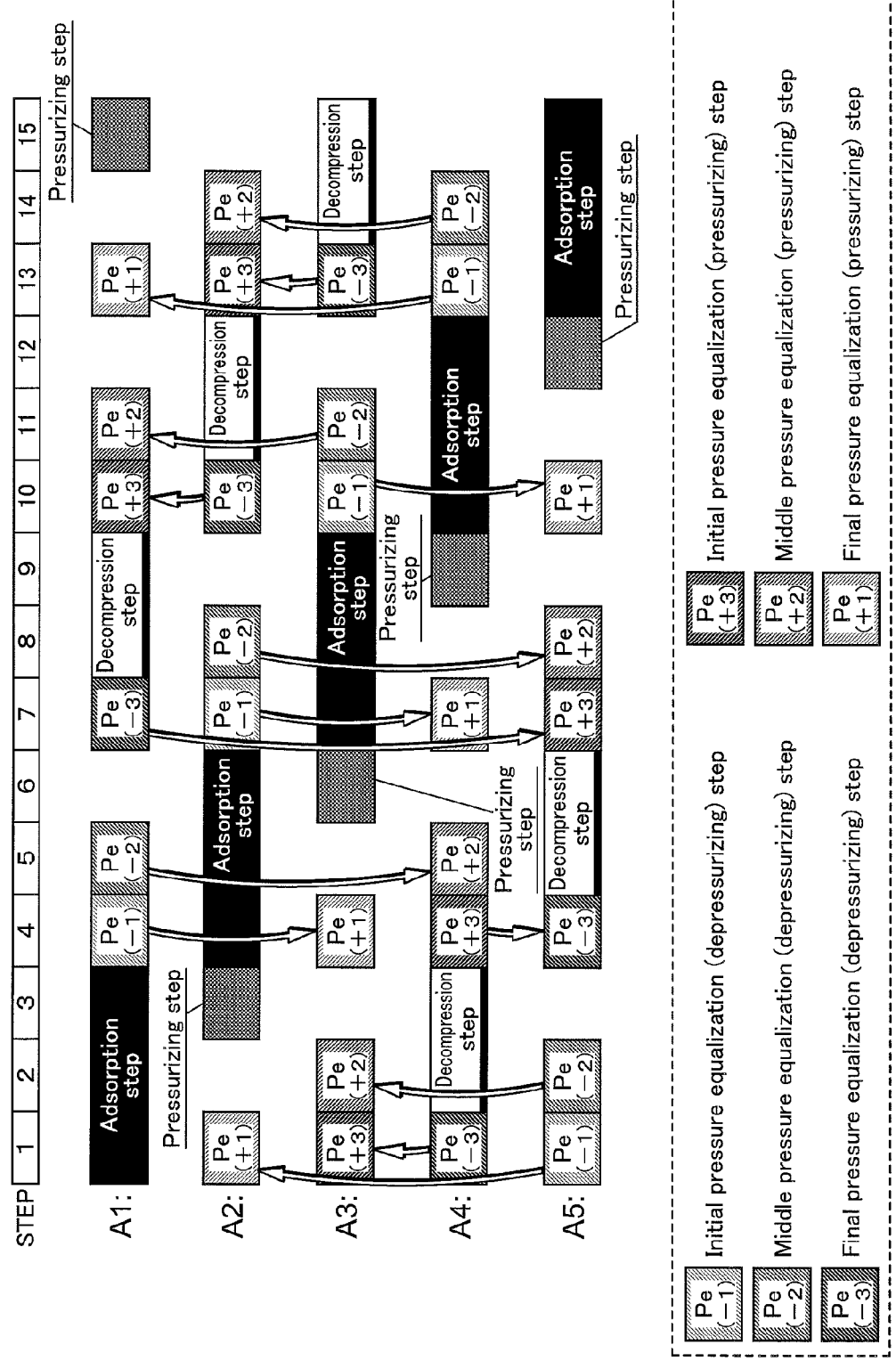
FIG. 11 is a diagram showing a methane concentration method performed by the methane concentration apparatus including five adsorption towers.

For example, in the case of using five adsorption towers, it is possible to adopt a configuration as shown in FIG. 10, and use the operation mode shown in FIGS. 11 and 12. Although the detailed description has been omitted here, the operation of the methane gas concentration method described in FIGS. 11 and 12 corresponds to the operation of the methane gas concentration method according to the embodiment shown in FIGS. 2 and 3. In FIGS. 10 to 12, the same configurations as those of the previous embodiment (FIGS. 1 to 3) are denoted by the same reference numeral and names, and the description thereof has been omitted. Here, as a difference from the previous embodiment, the pressure equalization (depressurizing) step and the pressure equalization (pressurizing) step will be described below.

Referring to FIG. 12, assuming that, as the intermediate pressure state between the high pressure state in which the adsorption step is performed and the low pressure state in which the decompression step is performed, first, second, and third pressure states in which the internal pressures of the adsorption towers are different are set and the pressure increases in this order, it can be seen that the operation of transferring the gas in one of the adsorption towers that is in the high pressure state to another one of the adsorption towers that is in an intermediate pressure state at a pressure lower than the pressure of the one of the adsorption towers so as to bring the pressure in the one of the adsorption towers into a high pressure-side intermediate pressure state corresponds to an initial pressure equalization (depressurizing) step of transferring, from one of the adsorption towers that is in the high pressure state, the gas in the adsorption tower to another one of the adsorption towers that is in the second pressure state so as to attain the first pressure state, and the operation of transferring, in the final pressure equalization (depressurizing) step, the gas in one of the adsorption towers that is in the high pressure-side intermediate pressure state at a pressure higher than the low pressure state to another one of the adsorption towers that is in the low pressure state so as to bring the pressure in the one of the adsorption towers into a low pressure-side intermediate pressure state corresponds to the final pressure equalization (depressurizing) step of transferring the gas from one adsorption tower that is in the second pressure state to another adsorption tower that is in the low pressure state so as to attain the third pressure state.

In addition, as a middle pressure equalization (depressurizing) step, a step of transferring the gas in one of the adsorption towers that is in the first pressure state to another one of the adsorption tower that is in the third pressure state so as to bring the pressure in the one of the adsorption towers into the second pressure state is included in the pressure equalization (depressurizing) step.

The same applies to the pressure equalization (pressurizing) steps.

INDUSTRIAL APPLICABILITY

The methane gas concentration method according to the present invention can be applied to recover methane gas from coal mine gas, which has hitherto been discarded, and to concentrate and reuse the methane gas.

DESCRIPTION OF REFERENCE SIGNS

1: Supply unit
2: Release unit
3: Recovery unit
4: Pressurizing unit
5: Pressure equalization unit
A1: First adsorption tower
A2: Second adsorption tower
A3: Third adsorption tower
A4: Fourth adsorption tower
C: Controller
L11: Supply line
L12: Release line
L13: Recovery line
L14: Pressurizing line
L15: Pressure equalization line L16: Lower pressure equalization line
L56: Advection line
P1: Supply pump
P3: Vacuum pump
T1: Source gas tank
T3: Product gas tank
V11 to V46: Switching valves

The invention claimed is:

1. A methane gas concentration method comprising providing four or more adsorption towers each filled with an adsorbent that adsorbs methane gas in a methane-containing gas and performing, for each of the adsorption towers, a PSA cycle comprising the following steps:
   (a) an adsorption step of receiving a supply of the methane-containing gas in a high pressure state near atmospheric pressure from a lower portion of an adsorption tower, adsorbing the methane gas on the adsorbent, and releasing non-adsorbed gas composed mainly of air from an upper portion of the adsorption tower;
   (b) a pressure equalization (depressurizing) step of transferring the non-adsorbed gas remaining in the adsorption tower that has finished the adsorption step and is in the high pressure state to another adsorption tower in a lower pressure state so as to bring the inside of the adsorption tower into an intermediate pressure state;
   (c) a decompression step of further decompressing the adsorbent in the adsorption tower that has finished the pressure equalization (depressurizing) step to a low pressure state so as to desorb the methane gas adsorbed on the adsorbent, and recovering said methane gas from the lower portion of the adsorption tower;
   (d) a pressure equalization (pressurizing) step of receiving, after finishing the decompression step, the non-adsorbed gas from another adsorption tower that is in a higher pressure state so as to bring the inside of the adsorption tower into an intermediate pressure state; and
   (e) a pressurizing step of, after an internal pressure of the adsorption tower has been increased by the pressure equalization (pressurizing) step, further supplying a pressurizing air into the adsorption tower from an upper portion of the adsorption tower so as to restore the adsorbent into the high pressure state capable of selectively adsorbing the methane gas,
   wherein the adsorbent has a property of selectively adsorbing the methane gas contained in the air in the high pressure state near atmospheric pressure and desorbing the adsorbed methane gas in the low pressure state, and a property of preferentially desorbing the air when desorbing the methane gas,
   wherein a plurality of different pressure states of the adsorption tower are set as the intermediate pressure states,
   wherein the pressure equalization (depressurizing) step includes:
   (b-i) an initial pressure equalization (depressurizing) step of transferring the non-adsorbed gas in the adsorption tower that is in the high pressure state to another one of the adsorption towers that is in an intermediate pressure state at a pressure lower than the high pressure state so as to bring the pressure in the the adsorption tower in the high pressure state into a high pressure-side intermediate pressure state; and
   (b-ii) a final pressure equalization (depressurizing) step of transferring the non-adsorbed gas in the adsorption tower that is in the high pressure-side intermediate pressure state at a pressure higher than the low pressure state to another one of the adsorption towers that is in the low pressure state so as to bring the pressure in the adsorption tower in the high pressure-side intermediate pressure state into a low pressure-side intermediate pressure state,
   wherein the pressure equalization (pressurizing) step includes:
   (d-i) an initial pressure equalization (pressurizing) step of receiving the non-adsorbed gas in one of the adsorption towers that is in the high pressure-side intermediate pressure state into the adsorption tower that is in the low pressure state so as to bring the pressure in the adsorption tower in the low pressure state into the low pressure-side intermediate pressure state; and
   (d-ii) a final pressure equalization (pressurizing) step of receiving, into the adsorption tower that is in the low pressure-side intermediate pressure state, the non-adsorbed gas in another one of the adsorption towers that is in the high pressure state so as to bring the pressure in the adsorption tower in the low pressure-side intermediate pressure state into the high pressure-side intermediate pressure state, and
   wherein the transferring of the non-adsorbed gas from one of the adsorption towers that performs the pressure equalization (depressurizing) step to another one of the adsorption towers that performs the pressure equalization (pressurizing) step consists of transferring the non-adsorbed gas from an upper portion of the one of the adsorption towers performing the pressure equalization (depressurizing) to an upper portion of the another one of the adsorption towers performing the pressure equalization (pressurizing).

2. The methane gas concentration method according to claim 1,
   wherein the pressure equalization (depressurizing) step is composed of an initial pressure equalization (depressurizing) step and a final pressure equalization (depressurizing) step, and the pressure equalization (pressurizing) step is composed of an initial pressure equalization (pressurizing) step and a final pressure equalization (pressurizing) step,
   the non-absorbed gas discharged from the upper portion of one of the adsorption towers in the initial pressure equalization (depressurizing) step is supplied to the upper portion of another one of the adsorption towers that performs the final pressure equalization (pressurizing), and
   the non-absorbed gas discharged from the upper portion of one of the adsorption towers in the final pressure equalization (depressurizing) step is supplied to another one of the adsorption towers that performs the initial pressure equalization (pressurizing) step.

3. The methane gas concentration method according to claim 1, wherein the methane-containing gas comprises at least one gas selected from coal mine gas, biogas, reformed gas, and natural gas.

4. The methane gas concentration method according to claim 1, wherein the adsorbent contains at least one selected from the group consisting of activated carbon, zeolite, silica gel, and an organometallic complex having an average pore diameter of 4.5 to 15 Å as measured by the MP method and having a methane gas adsorption amount under atmospheric pressure and at 298 K of 20 Nml/g or more.

* * * * *

UNITED STATES PATENT AND TRADEMARK OFFICE
CERTIFICATE OF CORRECTION

PATENT NO. : 9,944,575 B2
APPLICATION NO. : 14/772489
DATED : April 17, 2018
INVENTOR(S) : Shota Kawashima et al.

It is certified that error appears in the above-identified patent and that said Letters Patent is hereby corrected as shown below:

In the Claims

Column 21, Line 61, Claim 1, delete "the the" and insert -- the --

Signed and Sealed this
Twenty-fourth Day of July, 2018

Andrei Iancu
*Director of the United States Patent and Trademark Office*